United States Patent [19]

Cordi et al.

[11] Patent Number: 4,918,064

[45] Date of Patent: Apr. 17, 1990

[54] PHENYL GLYCINES FOR USE IN REDUCING NEUROTOXIC INJURY

[75] Inventors: Alex A. Cordi, St. Louis; Michael L. Vazquez, Ballwin, both of Mo.

[73] Assignee: G. D. Searle & Co., Chicago, Ill.

[21] Appl. No.: 111,749

[22] Filed: Oct. 21, 1987

[51] Int. Cl.$^4$ .............................. C07F 9/38; C07F 9/40; A01K 31/66
[52] U.S. Cl. .................................. 514/114; 558/178; 558/190; 562/11; 562/14; 564/14
[58] Field of Search ................. 260/502.50; 514/114; 558/178, 190; 562/11, 14; 564/14

[56] References Cited

U.S. PATENT DOCUMENTS 4,657,899 4/1987 Rzeszotarski et al. .............. 514/120
4,761,405 8/1988 Rzeszotarski et al. .............. 558/190

OTHER PUBLICATIONS

S. M. Rothman and J. W. Olney, *Annals of Neurology*, vol. 19, No. 2 (1986).
M. N. Perkins et al., *Neuroscience Lett.*, 23, 333 (1981).
J. Davies et al., *Neuroscience Lett.*, 21, 77 (1981).
K. Matoba et al., *Chem. Pharm. Bull.*, 32, (10) 3918–3925 (1984).
J. W. Olney et al., *Neuroscience Letters*, 68, 29–34 (1986).

*Primary Examiner*—Anton H. Sutto
*Attorney, Agent, or Firm*—J. Timothy Keane; Paul D. Matukaitis

[57] ABSTRACT

A class of phenyl glycine compounds is described for treatment to reduce neurotoxic injury associated with anoxia or ischemia which typically follows stroke, cardiac arrest or perinatal asphyxia. The treatment includes administration of a phenyl glycine compound alone or in a composition in an amount effective as an antagonist to inhibit excitotoxic actions at major neuronal excitatory amino acid receptor sites.

42 Claims, No Drawings

PHENYL GLYCINES FOR USE IN REDUCING NEUROTOXIC INJURY

FIELD OF THE INVENTION

This invention is in the field of clinical neurology and relates specifically to a class of compounds, compositions and methods for neuro-protective purposes such as controlling chronic or acute neurotoxic injury or brain damage resulting from neuro-degenerative diseases. For example, these compounds are particularly useful for treating neurotoxic injury which follows periods of anoxia or ischemia associated with stroke, cardiac arrest or perinatal asphyxia. The compounds would also be useful as anti-convulsants and analgesics.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman and J. W. Olney, "Glutamate and the Pathophysiology of Hypoxia - Ischemic Brain Damage," *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

Aminophosphonic acids have been investigated as neurotransmitter blockers [see M. N. Perkins et al, *Neuroscience Lett.*, 23, 333 (1981); and J. Davies et al, *Neuroscience Lett.*, 21, 77 (1981)]. In particular, compounds such as 2-amino-4-(2-phosphonomethylphenyl)-butyric acid and 2-(2-amino-2-carboxy)ethylphenylphosphonic acid have been synthesized for evaluation as antagonists in blocking the action of the neurotransmitter compounds L-glutamic acid and L-aspartic acid [K. Matoba et al, "Structural Modification of Bioactive Compounds II. Syntheses of Aminophosphonic Acids", *Chem. Pharm. Bull.*, 32, (10) 3918–3925 (1984)].

U.S. Pat. No. 4,657,899 to Rzeszotarski et al described a class of ω-[2-(phosphonoalkylenyl)phenyl]-2-aminoalkanoic acids characterized as being selective excitatory amino acid neurotransmitter receptor blockers. These compounds are mentioned for use as anticonvulsants, antiepileptics, analgesics and cognition enhancers. Typical compounds of the class include 3-[2-phosphonomethylphenyl]-2-aminopropanoic acid and 3-2-(2-phosphonoethyl)phenyl]-2-aminopropanoic acid.

Other classes of compounds have been tested as agonists in blocking NMDA- or KA-induced neurotoxicity [J. W. Olney et al., "The Anti-Excitotoxic Effects of Certain Anesthetics, Analgesics and Sedative-Hypnotics", *Neuroscience Letters*, 68, 29–34 (1986)]. The tested compounds included phencylidine, ketamine, cyclazocine, kynurenate and various barbiturates such as secobarbital, amobarbital and pentobarbital.

DESCRIPTION OF THE INVENTION

Control of neuropathological processes and the neurodegenerative consequences thereof in mammals is provided by treating a mammal susceptible to neurotoxic injury with an anti-excitotoxic compound provided by an effective amount of a neuroreceptor antagonist. The anti-excitotoxic compound is characterized in having activity as an antagonist at a major neuronal excitatory amino acid receptor site. This class of phenyl glycine NMDA antagonist compounds is also expected to contain compounds having anti-convulsant and analgesic activity. Such NMDA antagonist compounds may be selected from a class of phenyl glycine compounds defined by Formula I:

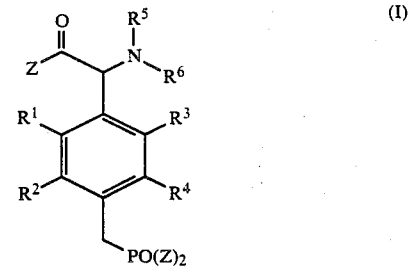

wherein each of $R^1$ through $R^4$ is independently selected from hydrido, alkyl, cycloalkyl, aralkyl, aryl, haloalkyl, halo, cyano, nitro, and groups represented by $-OR^5$, $-SR^5$,

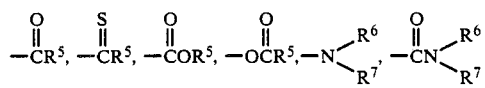

wherein $R^5$ is selected from hydrido, alkyl, aryl, and aralkyl; and wherein each of $R^5$ and $R^7$ is independently selected from hydrido alkyl, acyl, aryl, aralkyl and

and wherein Z is selected from $-OR^5$, $-SR^5$,

and

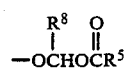

wherein each of $R^5$, $R^6$ and $R^7$; is defined as before; and wherein $R^8$ is selected from hydrido and alkyl; with the proviso that $R^6$ and $R^7$ are not at the same time carbonyl-containing groups. Within this class of phenyl glycines of the invention are the pharmaceutically acceptable salts of the compounds of Formula I, including acid addition salts, base addition salts including alkali metal salts. Also included within this class of phenyl glycine compounds of the invention are tautomeric forms of the defined compounds and isomeric forms including diastereomers and enantiomers.

A preferred class of compounds within Formula I comprises those compounds wherein Z is hydroxyl. Within this class is a more preferred class of compounds of Formula I wherein $R^6$ is hydrido. More highly preferred are those compounds wherein one or more of $R^1$, $R^2$, $R^3$ and $R^4$ is hydrido. Even more preferred within this class of compounds are those compounds wherein two or more of the $R^1$, $R^2$, $R^3$ and $R^4$ are hydrido. Still more highly preferred within this class are compounds wherein three or more of $R^1$, $R^2$, $R^3$ and $R^4$ are hydrido. Most preferred are those compounds of Formula I wherein each of $R^1$, $R^2$, $R^3$, $R^4$ and $R^5$ is hydrido.

Another preferred class of compounds within Formula I comprises those compounds wherein each of $R^1$, $R^2$, $R^3$ and $R^4$ is independently selected from hydrido, halo, alkyl, alkoxy and thioalkoxy. More preferred within this class are compounds wherein two or more of $R^1$, $R^2$, $R^3$ and $R^4$ are hydrido. More highly preferred within this class are those compounds of Formula I wherein three or more of $R^1$, $R^2$, $R^3$ and $R^4$ are hydrido. Most preferred within this class are compounds of Formula I wherein each of $R^1$, $R^2$, $R^3$ and $R^4$ is hydrido.

An example of a specific, most highly preferred compound within Formula I is 4-(phosphonomethyl)-phenylglycine. This compound exists as a racemic mixture, or as the dextro- and levo-isomers. Also, this compound may be in the form of a salt, including alkali metal salts such as the sodium salt.

The term "hydrido" denotes a single hydrogen atom (H) which may be attached, for example, to a carbon atom or to an oxygen atom to form an hydroxyl group. Where the term "alkyl" is used, either alone or within other terms such as "haloalkyl", "aralkyl" and "hydroxyalkyl", the term "alkyl" embraces linear or branched radicals having one to about ten carbon atoms. Preferred alkyl radicals are "lower alkyl" radicals having one to about five carbon atoms. The term "cycloalkyl", embraces radicals having three to ten carbon atoms, such as cyclopropyl and cyclobutyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as bromochloromethyl group. Examples of a polyhaloalkyl are trifluoromethyl, 2,2,2-trifluoroethyl, perfluoroethyl and 2,2,3,3-tetrafluoropropyl groups. The term "thioalkyl", as represented by the fragment $-SR^5$, embraces radicals containing a linear or branched alkyl group, each of one to about ten carbon atoms to a divalent sulfur atom. The term "alkoxy", as represented by the fragment $-OR^5$, embraces linear or branched oxy-containing radicals having an alkyl portion of one to about ten carbon atoms, such as a methoxy group. The term "aryl" embraces aromatic radicals such as phenyl and naphthyl. The term "aralkyl" embraces aryl-substituted alkyl radicals such as benzyl, diphenylmethyl and triphenylmethyl. The terms "benzyl" and "phenylmethyl" are interchangeable. The term "pharmaceutically-acceptable salts" embraces salts commonly used to form alkali metal salts and to form addition salts of free acids or free bases. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulphuric acid and phosphoric acid and such organic acids as maleic acid, succinic acid and citric acid. Other salts include salts with alkali metals or alkaline earth metals, such as sodium, potassium, calcium and magnesium, or with organic bases, such as dicyclohexylamine. All of these salts may be prepared by conventional means from the corresponding compound of Formula I by reacting, for example, the appropriate acid or base with the compound of Formula I.

Other examples of specific compounds of Formula I are the following:
2,5-dichloro-4-phosphonomethylphenylglycine;
2,5-dimethyl-4-phosphonomethylphenylglycine;
2-bromo-4-phosphonomethylphenylglycine;
3-bromo-4-phosphonomethylphenylglycine;
ethyl 4-phosphonomethylphenylglycine phosphonic ester;
2,3,5,6-tetrafluoro-4-phosphonomethylphenylglycine;
N-methyl-4-phosphonomethylphenylglycine;
N-benzyl-4-phosphonomethylphenylglycine;
(D) 4-phosphonomethylphenylglycine.

Compounds of Formula I may be prepared in accordance with the following general procedures:

Generic Procedure I

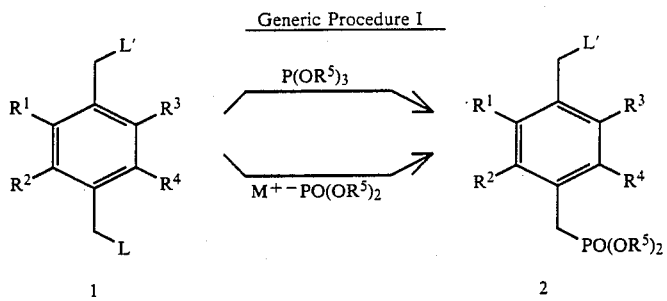

wherein each of L,L' is independently halogen, tosylate, mesylate, brosylate, OH, acetal, aldehyde, acid, or ester; $R^1$–$R^4$ as defined before; $R^5$ = lower alkyl, phenyl, or benzyl; $M^+$ = $Na^+$, $K^+$, $Li^+$, or $Mg^{++}$.

One of the processes which can be used to synthesize the products of the invention starts with para-xylenes of the general formula 1 where $R^1$, $R^2$, $R^3$ and $R^4$ have the values defined previously. L and L' can be the same or different, as long as at least one of L and L' is a good leaving group. Good leaving groups are, for example, halogen, tosylate, mesylate and brosylate. These para-xylene derivatives may be treated either with a trisubstituted phosphite of the general formula $P(OR^5)_3$ where $R^5$ can be lower alkyl, aryl or benzyl, or with the metallic salt of a disubstituted phosphite of the general formula $M$—$PO(OR^5)_2$ wherein $M^+$ represents a metallic cation such as $Na^+$, $K^+$, $Li^+$, or $Mg^{++}$, to generate the desired mono-disubstituted phosphono-xylene of general formula 2. The reaction is best achieved by mixing appropriate quantities of the reagents either neat or in a solvent like toluene, tetrahydrofuran, ether, or a lower alcohol, according to the solubility of the two reagents, and the reaction temperature can vary from about 0° C. to reflux of the reaction mixture.

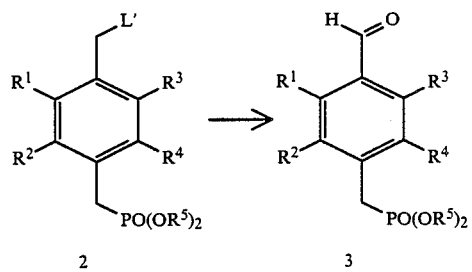

wherein L' and $R^1$–$R^5$ are as defined before.

In the second step of the process, the group L' is transformed into an aldehyde group. If L' is a leaving group, it can be hydrolyzed in the presence of water and an inorganic base such as $CaCO_3$, $Ca(OH)_2$, or NaOH, and the resulting alcohol can be oxidized to the aldehyde by an inorganic oxidant such as $MnO_2$, $K_2CrO_7$, or pyridinium chlorochromate in solvents such as dioxane or dichloromethane. Other ways to perform this transformation are heating compound 2 in dimethylsulfoxide (DMSO), or treating it with dimethylaminopyridine N-oxide in the presence of tert-butylate anion, or with sodium thiophenoxide in the presence of thioisocyanate anion or with di(tetrabutylammonium)chromate or any other oxidant familiar to those skilled in the art.

If L' is an acetal, cyclic or acyclic, the aldehyde functionality can be generated by hydrolyzing in the water in the presence of an acidic catalyst such as trifluoroacetic acid, acetic acid, para-toluenesulfonic acid or any other organic or mineral acid. The aldehyde can also be prepared by transketalization in the presence of excess aldehyde and the same acidic catalysts.

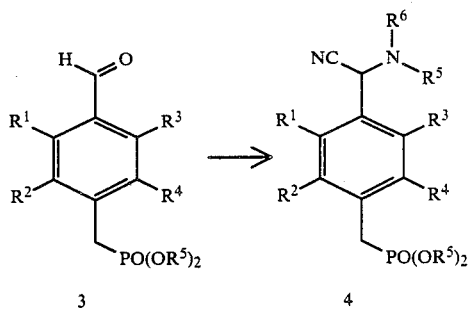

wherein each of $R^5$ and $R^6$ is independently selected from H, lower alkyl, benzyl, trityl, and diphenylmethyl.

The aldehyde 3 is transformed into an amino nitrile by treating it in a protic or aprotic solvent with an amine $R^5R^6NH$, wherein each of $R^5$ and $R^6$ independently represents hydrido, lower alkyl, benzyl, trityl or diphenylmethyl, and a cyanide delivering compound such as, metallic cyanide, trimethylsilyl cyanide or diethylcyanophosphate. It is particularly advantageous to conduct the reaction in acetonitrile in the presence of ammonium chloride, potassium cyanide and alumina while the reaction mixture is irradiated with ultrasound.

Alternatively, the aldehyde can be condensed first with the amine under conditions where water is excluded to form the imine. Then the imine is treated with a cyanide carrier optionally in the presence of a suitable catalyst when required.

The aldehyde 3 can also be transformed into an hydantoin, for example, by treating it with an amine, $R^6NH_2$ of the type described above, $CO_2$ and a cyanide carrier.

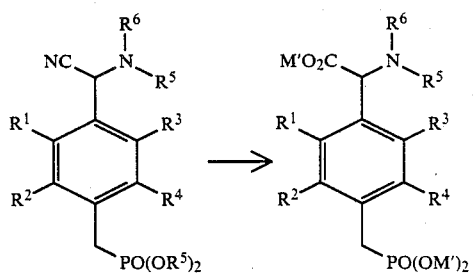

wherein $M' = H^+, Na^+, K^+, Li^+, Ca^{++}, Ba^{++}, Cs^+$.

The amino nitriles 4 as well as the hydantoin can be hydrolyzed by heating in an aqueous solution containing an inorganic acid such as HCl, HBr, $H_2SO_4$, or containing an inorganic base such as NaOH, KOH, $Ba(OH)_2$ or $Ca(OH)_2$.

Generic Procedure II

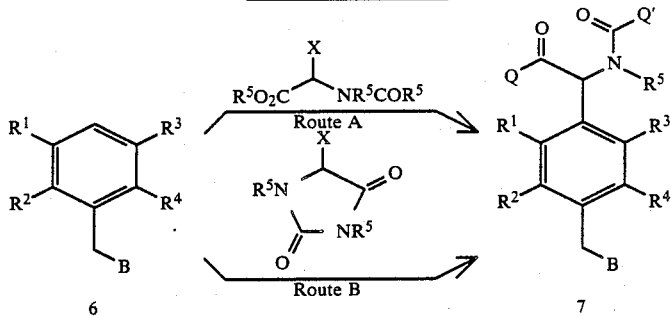

wherein $R^1$–$^5$ are as previously defined; B=L, but also includes

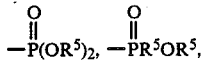

$P(R^5)_2$; X=OH, halogen, tosylate, mesylate, brosylate or other leaving groups; by Route A, $Q=OR^5$, $Q'=R^5$; by Route B, $Q=Q'=NR^5$.

The products of the invention may be prepared by condensing an appropriately substituted aromatic compound 6 with either a glycine or hydantion derivative as described above. The condensation may utilize either Lewis or Bronsted acids as catalysts. In some instances the acids may also serve as solvents for the reaction. Combinations of acids, such as acetic and sulfuric, may also be used. The reaction may be carried out at 0° C. up to 100° C., but is preferably done at room temperature. When $B=PO(OR^5)_2$ the target compounds are obtained directly.

Generic Procedure III

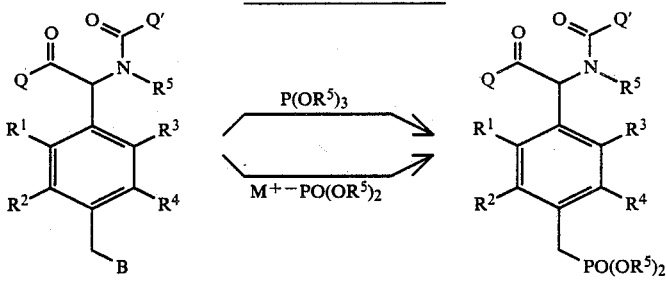

where $R^1$-$R^5$, B, Q and Q' are as defined before.

When B is hydroxyl it may be converted into a leaving group such as halogen, tosylate, mesylate, brosylate, or other good leaving group using techniques familiar to those skilled in the art. The leaving group may be transformed into a phosphorus-containig moiety as previously described.

The free amino acids and their salts may be obtained by acidic or basic hydrolysis as previously described. When $R^5$ is benzyl, and Q is $OR^5$ and Q' is Q, the free amino acids may be obtained by hydrogenation using techniques familiar to those skilled in the art The following Examples I-X are detailed descriptions of the methods of preparation of compounds of Formula I. These detailed preparations fall within the scope of, and serve to exemplify, the above described Generic Procedures which form part of the invention. These Examples I-X are presented for illustrative purposes only and are not intended as a restriction on the scope of the invention. All parts are by weight unless otherwise indicated. Most of the commercially-available starting materials were obtained from Aldrich Chemical Co., Milwaukee, Wis.

EXAMPLE I

α-Bromo-α'-diethylphosphono-p-xylene

α,α'-Dibromo-p-xylene (22.9 gm) was combined with toluene (70 mL) and heated to reflux. Once the dibromide had completely dissolved, triethylphosphite (5.9 mL) was added all at once and heating continued for 6 hours. The reaction mixture was allowed to cool to room temperature and the excess solid dibromide was removed by suction filtration and washed with a small amount of methylene chloride. The organic solutions were combined and concentrated, on a rotatory evaporator, to a white solid. The solid was taken up in methylene chloride (50 mL) and chromatographed on silica (350 gm). The column was eluted with methylene chloride and fractions of about 25 mL were collected The first peak eluted in fractions 14-24 (excess dibromide), then the solvent was changed to 5% ethanol/methylene chloride. The second major peak, fractions 37-53, was the desired product obtained as a pale yellow oil.

EXAMPLE II 4-(Diethylphosphonomethyl)benzaldehyde

DMSO (68 mL) was heated to 100° C. (oil bath temp=120° C.) and then $NaHCO_3$ (9.73 gm) was added all at once. The mixture was stirred well as α-bromo-α'- diethylphosphono-p-xylene (4.75 gm) in DMSO (5 mL) was quickly added. The mixture was stirred for 6 min. and then quickly cooled to room temperature. The reaction mixture was combined with $H_2O$ (400 mL) and extracted with $3 \times 100$ mL $CH_2Cl_2$. The combined organic layers were washed with $2 \times 100$ mL $H_2O$ and dried over $MgSO_4$. Filtration and concentration produced a clear oil (4.84 gm). The material was taken up in $CH_2Cl_2$ and applied to a silica gel column (175 gm) previously saturated with 5% ethanol/$CH_2Cl_2$. The column was eluted with 5% ethanol/$CH_2Cl_2$ and 25 mL fractions were collected. The product eluted in fractions 30–63. It was preceded by 2 small peaks and followed by one minor peak. The product was obtained as a clear oil.

EXAMPLE III 4-(Diethyl phosphonomethyl)benzoic acid

Triethyl phosphite (155 mmol) and α-bromo-p-toluic acid (140 mmol) were combined with toluene (75 mL) and heated to reflux for 18 hours. The reaction was allowed to slowly cool to room temperature. The product which crystallized from the solution was collected by suction filtration, washed with petroleum ether and dried under reduced pressure. The product was obtained as a pure white crystalline solid.

EXAMPLE IV 4-(Diethyl phosphonomethyl)benzyl alcohol 4-(Diethyl phosphonomethyl)benzoic acid (66 mmol) was suspended in anhydrous THF (75 mL) under a nitrogen atmosphere. The reaction was cooled in an ice bath while diborane 1M in THF (72.6 mmol) was added dropwise to the acid. Once the addition was complete the reaction was allowed to gradually warm to room temperature over several hours. The reaction was quenched by the careful addition of $H_2O$ (50 mL), then most of the THF was removed on a rotatory evaporator. The residue was partitioned between dichloromethane (100 mL) and $H_2O$ (100 mL). The layers were separated and the aqueous later extracted a second time with dichloromethane (100 mL). The combined organic layers were washed with $H_2O$ (100 mL), dried ($MgSO_4$), and concentrated to give the product as a clear oil.

EXAMPLE V 4-(Diethyl phosphonomethyl)benzaldehyde

Pyridinium chlorochromate (110 mmol) in dichloromethane (150 mL) was rapidly stirred while 4-(diethyl phosphonomethyl)benzyl alcohol (73.6 mmol) in dichloromethane (15 mL) was rapidly added. After 1.5 hours, ethyl ether (200 mL) was added to the reaction mixture and the organic solution was decanted from the tarry residue. The residue was washed with $3 \times 50$ mL ethyl ether. The combined organic solution was filtered through Florisil chromatographic material and concentrated to a brown oil. The oil was then distilled to give the product as a clear oil (BP 150°–180° C. @0.002–0.005 mm Hq).

EXAMPLE VI 4-(Phosphonomethyl)phenylglycine

A mixture of KCN (651 mg), $NH_4Cl$ (588 mg), Merck neutral alumina (1.5 gm) in acetonitrile (15 mL) was irradiated with ultrasound at 50° C. for 10 minutes. To this mixture was then added 4-(diethyl phosphonomethyl)benzaldehyde (1.28 gm) and the mixture was irradiated with ultrasound for 24 hours. The excess salts and alumina were removed by filtration through Celite filtration aid and the resulting solution was concentrated on a rotatory evaporator to an oil which was identified as α-amino-4-(diethyl phosphonomethyl)phenylacetonitrile [δ1.25 (3H,t), 3.18 (2H,d), 4.02 (2H,p), 4.90 (1H,t), 7.40 (4H,m), relative to TMS]. The oil was taken up in 6N HCl (10 mL) and heated to reflux for 24 hours, then concentrated to a solid on a rotatory evaporator. The material was purified by ion exchange chromatography on Amberlite IR 120 (H+form) resin. The material was applied to a column ($1 \times 15$ cm) and eluted with water until the effluent was about pH=6. The column was then eluted with 1N pyridine (200 mL). The effluent was concentrated on a rotatory evaporator and the resulting solid was recrystallized from ethanol-water to give the product as a white solid. Analytical data are reported in Table I.

EXAMPLE VII 4-(Ethyl phosphonomethyl)phenylglycine

Crude material prepared according to the method of Example VI was applied to a $1 \times 15$ cm Dowex-1 $8 \times 200$ resin column (OH- form) and eluted with water to remove any neutral materials. The eluent was changed to 1N acetic acid, whereupon the mono-phosphonoethyl ester of 4-(phosphonomethyl)phenylglycine eluted. The product was concentrated to dryness on a rotatory evaporator and the resulting solid recrystallized from ethanol/water to give the product as a white solid. Continued elution of the column with 1 N HCl affords the product of Example VI as the HCl salt. Increased quantities of the mono-phosphonoethyl ester may be isolated from the crude product of Example VI by heated at reflux in 6N HCl. Analytical data are reported in Table I.

EXAMPLE VIII

α-Chloro-α'-diethylphosphono-2,5-dimethyl-p-xylene 2,5-Bis(chloromethyl)-p-xylene (25 mmol) and triethylphosphite (10 mmol) were combined and heated to 130° C. under a nitrogen atmosphere for 24 hours. The reaction mixture was chromatographed on silica gel (175 gm). The column was eluted with dichloromethane until the excess starting material eluted. The eluting solvent was then changed to 5% ethanol/dichloromethane whereupon the product eluted The appropriate fractions were pooled and concentrated on a rotatory evaporator to give the product as an oil.

EXAMPLE IX 2,5-Dimethyl-4-(diethylphosphonomethyl)benzaldehyde

DMSO (32 mL) was heated to 100° C. and then $NaHCO_3$ (4.5 gm) was added all at once. The mixture was stirred vigorously as α-chloro-α'-diethylphosphono-2,5-dimethyl-p-xylene (7 mmol) in DMSO (45 mL) and chloroform (5 mL) was rapidly added. The mixture was stirred for 7 min. and then quickly cooled to room temperature. The reaction mixture was combined with $H_2O$ (350 mL) and extracted with $3 \times 125$ mL ethyl ether. The combined organic layers were washed with $5 \times 150$ mL $H_2O$, dried over $MgSO_4$, and concentrated on a rotatory evaporator to an oil. The crude material was chromatographed on silica gel (175 gm) using ethyl acetate as the eluting solvent. The appropriate fractions were pooled and concentrated to give the product as a clear oil.

EXAMPLE X 2,5-dimethyl-4-(phosphonomethyl)phenylglycine hydrochloride

A mixture of KCN (190 mg), NH₄Cl (175 mg), and Merck neutral alumina (440 mg) in acetonitrile (5 mL) was irradiated with ultrasound at 50° C. for 10 minutes. 2,5-Dimethyl-4-(diethyl phosphonomethyl)benzaldehyde (420 mg) in CH₃CN (5 mL) was then added and the mixture irradiated with ultrasound for 24 hours. The excess salts and alumina were removed by filtration through Celite filtration aid and the resulting solution was concentrated on a rotatory evaporator to an oil which was identified as α-amino-2,5-dimethyl-4-(diethyl phosphonomethyl) phenylacetonitrile. The oil was taken up in 6N HCl (10 mL) and heated to reflux for 24 hours, then concentrated to dryness on a rotatory evaporator. The solid was taken up in water (20 mL) and applied to an Amberlite IR-120 (H+ form) resin column (1×20 cm). The column was eluted with water until the eluent was neutral, then with 1N pyridine. The pyridine effluent was concentrated to dryness on a rotatory evaporator. The resulting solid was taken up in H₂O (20 mL) and applied to a Dowex-1 8×200 (OH— form) resin column (1×20 cm). The column was eluted with water, then 1N acetic acid, and finally with 1N HCl whereupon the product eluted. The appropriate fractions were pooled and concentrated to dryness. The solid was then recrystallized from ethanol/water to give the product as a white solid. Analytical data are reported in Table I.

TABLE I

Product Compounds

| Example No. | Structure | Product Analysis Theory | Found | NMR Data* |
|---|---|---|---|---|
| VI | 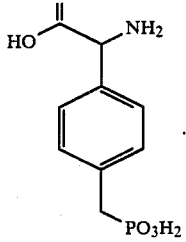 .0.85 H₂O | C 41.50<br>H  5.30<br>N  5.38 | 41.70<br>4.88<br>5.16 | δ 2.99 (2H,d)<br>4.81 (1H,s)<br>7.27 (4H,s) |
| VII | 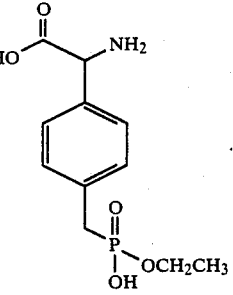 .0.50 H₂O | C 46.81<br>H  6.07<br>N  4.96 | 47.05<br>5.84<br>4.75 | δ 1.14 (3H,t)<br>2.98 (2H,d)<br>4.21 (2H,m)<br>5.15 (1H,s)<br>7.32 (4H,s) |
| X | 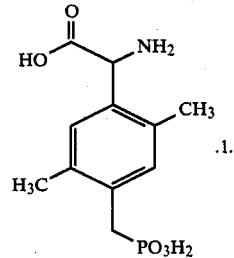 .1.5 H₂O HCl | C 39.36<br>H  5.70<br>N  4.17 | 39.66<br>5.20<br>4.07 | δ 2.20 (3H,s)<br>2.25 (3H,s)<br>3.02 (2H,d)<br>7.05 (2H,d) |

*relative to HOD peak @ 6.65 ppm

BIOLOGICAL EVALUATION

Binding Assays:

[Pullan, L. M., Olney, J. W., Price, M. T., Compton, R. P., Hood, W. F., Michel J., Monahan J. B., "Excitatory Amino Acid Receptor Potency and Subclass Specificity of Sulfur-Containing Amino Acids", *Journal of Neurochemistry*, 49 1301–1307, (1987)].

Synaptic plasma membranes (SPM) were prepared as previously described [Monahan, J. B. and Michel, J., "Identification and Characterization of an N-methyl-D-aspartate-specific L[³H]glutamate Recognition Site in Synaptic Plasma Membranes, *J. Neurochem.*, 48, 1699–1708 (1987)]. The SPM were stored at a concentration of 10–15 mg/ml in 0.32M sucrose, 0.5 mM EDTA, 1 mM MgSO₄, 5 mM Tris/SO₄, pH 7.4, under liquid nitrogen. The identity and purity of the subcellular fractions were confirmed by both electron microscopy and marker enzymes. Protein concentrations were determined by using a modification of the method of Lowry [Ohnishi, S. T. and Barr, J. K., "A Simplified Method of Quantitating Proteins Using the Biuret and Phenol Reagents", *Anal. Biochem.*, 86, 193–197 (1978)].

The SPM were treated identically for the [$^3$H]AMPA (QUIS), [$^3$H]kainate and sodium-dependent L-[$^3$H]-glumatate binding assays. The SPM were thawed at room temperature, diluted twenty-fold with 50 mM Tris/acetate, pH 7.4, incubated at 37° C. for 30 minutes, and centrifuged at 100,000 g for 15 minutes. The dilution, incubation, and centrifugation was repeated a total of three times.

Prior to use in the NMDA-specific L-[$^3$H]glutamate binding assay the SPM were thawed, diluted twenty fold with 50 mM Tris/acetate, pH 7.4 containing 0.04% (v/v) Triton X-100, incubated for 30 minutes at 37° C. and centrifuged as described above. The Triton X-100 treated membranes were washed with 50 mM Tris/acetate, pH 7.4 and centrifuged at 100,000 g for 15 minutes a total of four times. Triton X-100 treatment of the SPM resulted in a higher affinity and more consistency in this L-[$^3$H]glutamate binding assay. For this reason the $K_d$ for glutamate and the $K_i$ values for other compounds are lower than previously reported; however the pharmacological profile of this binding site was unaltered.

The basic procedure for the receptor subclass binding assays was similar. This general method involved adding the radioligand (12.5 nM L-[$^3$H]glutamate; 0.5 nM [$^3$H]kainate or 10 nM [$^3$H]AMPA) to the appropriate concentration of the test compound and initiating the assay by the addition of ice cold synaptic plasma membranes (0.2–0.45 mg). The binding assays were performed in 1.5 mL centrifuge tubes with the total volume adjusted to 1.0 mL. Additions of test compounds were made in 50 mM Tris/acetate, pH 7.4 and incubations were carried out at 0°–4° C. The incubation time for the NMDA and the AMPA binding assays was 10 minutes, for the kainate binding assay 60 minutes and for the sodium-dependent glutamate binding assay 15 minutes. The AMPA binding assay contained 100 mM KSCN and the sodium-dependent glutamate binding assay contained 150 mM sodium acetate in addition to the previously described reagents.

To terminate the incubation, the samples were centrifuged for 15 minutes at 12,000 g and 4° C. in a Beckman Microfuge 12. The supernatant was aspirated and the pelleted membranes dissolved in Beckman BTS-450 tissue solubilizer for a minimum of 6 hours at room temperature. Beckman MP scintillation cocktail containing 7 mL/1 acetic acid was then added and the samples counted on a Beckman LS 5800 or 3801 liquid scintillation counter with automatic corrections for quenching and counting efficiency.

Nonspecific binding was defined as the residual binding in the presence of either excess L-glutamate (0.1–0.4 mM), kainate (0.01 mM), or NMDA (0.5 mM), and was 15–25% of the total binding in the NMDA binding assay, 19–27% in the AMPA binding assay, 20–30% in the kainate binding assay and 10–15% in the sodium-dependent binding assay. Radioligand binding to the synaptic plasma membranes was analyzed using Scatchard and Hill transformations and the $K_i$ values of the compounds determined using logit-log transformations. Calculations and regression analysis were performed using templates developed for Lotus 1, 2, 3 as previously described [Pullan, L. M. "Automated Radioligand Receptor Binding Analysis with Templates for Lotus", *Computer Appln. Biosci.*, 3 131 (1987)]. Binding results are reported in Table II for example compounds of the invention. Included in Table II are binding data for D,L-AP7[D,L-2-amino-7-phosphonoheptanoic acid].

TABLE II

| | RECEPTOR BINDING DATA | | |
|---|---|---|---|
| | Binding (μM) | | |
| Compound | NMDA | KA | Quis |
| D,L-AP7 | 5.4 | >300 | >300 |
| D-AP7 | 4.0 | >300 | >300 |
| Ex. VI | 3.9 | >300 | >300 |
| Ex. VII | 70 | >300 | >300 |
| Ex. X | 21.3 | >300 | >300 |

In Vitro Chick Retina Assay

[Olney, J. W., Price, M. T., Fuller, T. A., Labruyere, J., Samson, L., Carpenter, M., Mahan, K., "The Anti-Excitotoxic Effects of Certain Anesthetics, Analgesics and Sedative-Hypnotics", *Neuroscience Letters*, 68, 29–34, (1986)].

Using an approach similar to that earlier described [Reif-Lehrer, L., Bergenthal, J. and Hanninen, L., "Effects of Monosodium Glutamate on Chick Embryo Retina in Culture", *Invest. Ophthalmol.*, 14, 114–12, (1975)], 15-day-old chick embryos were decapitated and their eyes removed and cut into quadrants after excising the cornea and removing the lens, vitreous and iris. The retinal quadrants were then gently separated from the pigment epithelium and incubated for 30 minutes at 37° C. in a standard balanced salt solution (BSS) to which test compounds, either excitatory amino acid agonists or potential antagonists or both, were added in various concentrations. As described elsewhere [Olney, J. W., Price, M. T., Samson, L. and Labruyere, J., "The Role of Specific Ions in Glutamate Neurotoxicity". *Neurosci. Lett.* 65, 65–71, (1986); Price, M. T., Olney, J. W., Samson, L. and Labruyere, J., "Calcium Influx Accompanies But Does Not Cause Excitotoxin-Induced Neuronal Necrosis", *Brain Res. Bull.*, 14, 369–376, (1985)], the BSS contained 140 mM Na$^+$, 5.0 mM K+, 0.5 mM Ca$^{2+}$, 4.5 mM Mg$^{2+}$, 150 mM Cl$^-$ and bicarbonate/-phosphate buffer (pH 7.3). After incubation for 30 minutes, the retinal quadrants were fixed by immersion in phosphate-buffered solution containing 1.5% glutaraldehyde and 1% paraformaldehyde, then additionally fixed in 1% osmium tetroxide and embedded in araldite, allowing sections to be cut for either light or electron microscopy [Olney, J. W., "Glutamate-Induced Retinal Degeneration in Neonatal Mice. Electron Microscopy of the Acutely Evolving Lesion", *J. Neuropathol. Exp. Neurol.*, 28, 455–474, (1969)].

In pilot studies [Samson, L., Olney, J. W., Price M. T. and Labruyere, J., "Kynurenate Protects Against Excitotoxin-Induced Neuronal Neorosis In Chick Retina", *Soc. Neurosci. Abstr.*, 10, 24, (1984)], it was determined that when the 15-day-old chick embryo retina is incubated for 30 minutes in BSS containing 1 mM Glu, a fully developed lesion occurs resembling that described in the immature mouse retina following s.c. administration of Glu. Other excitotoxin agonists were also found to produce acute lesions within 30 minutes, each agent being effective at a concentration proportional to its known excitatory and toxic potencies (e.g., kainate>-quisqualate>N-methyl-D-aspartate>Glu=Asp). The pattern of cellular degeneration was restricted in each case to the ganglion cell, inner plexiform and inner nuclear layers, but within these areas certain agonists induced different patterns of degeneration, the differences being most pronounced between NMDA and KA which we regard as prototypic molecules for inducing distinctive patterns of excitotoxic degeneration. For purposes of the present study, NMDA and KA were the agonists employed and numerous potential antagonists were tested at various concentrations for their ability to prevent NMDA or KA neurotoxicity. The concentrations of NMDA and KA used, 200 and 25 $\mu$M, respectively, were those found in pilot experiments to be the lowest concentrations required to consistently obtain fully developed retinal lesions. Although partial blocking was observed for each effective antagonist at concentrations below the threshold for complete protection, the criterion used for comparing agents for antagonist potency is the concentration required to completely prevent NMDA (200 $\mu$M) or KA (25 $\mu$M) from exerting any toxic activity in any specimen (n>6) studied at that concentration. Internal controls on each experiment consisted of at least 6 specimens being incubated with agonist alone (NMDA 200 $\mu$M or KA 25 $\mu$M). A typical toxic reaction had to be present in all controls and absent from all experimental specimens in order to qualify as a blocking effect. Results: Example VI: full antagonist against NMDA at 50 $\mu$M.

In Vitro Hippocampal Slice Assay

Hippocampal slices were prepared from male, Sprague-Dawley albino rats (100-300 gm) and maintained as described previously [Ganong, A. H., Lanthorn, T. H., Cotman, C. W., "Kynurenic Acid Synaptic and Acidic Amino Acid-Induced Responses in the Rat Hippocampus and Spinal Cord", *Brain Research*, 273 170-174 (1983)]. The hippocampus was removed in the cold and sliced to a thickness of 450 microns on a McIlwain tissue chopper in experimental medium (124 mM NaCl, 2.5 mM KCl, 1.0 mM KH$_2$PO$_4$, 26.4 mM NaHCO$_3$, 2 mM CaCl$_2$, 1.5 mM MgSO$_4$, and 10 mM D-glucose) with 10 mM Hepes. The slices were quickly transferred to a static bath and rinsed with experimental medium (without Hepes) and maintained at 34°-35° C. in a humidified chamber with 95% oxygen and 5% carbon dioxide. As needed, slices were transferred from the static bath to a small perfusion chamber where they were secured with an upper net and completely submerged in a continuously flowing experimental medium (2.0 ml/min). The Schaffer collateral/commissural-CA1 (S/C-CA1) synaptic response was stimulated (0.05 Hz; 0.01 msec. single duration shock) with bipolar electrodes (Rhodes, Inc.) from stratum radiatum at the CA2-CA3 border. Evoked field EPSPs and drug-induced focal potentials were recorded in the middle portion of CA1. Focal potentials were induced by pressure ejections of 100 $\mu$M NMDA, 100 $\mu$M K.A., and 100 $\mu$M AMPA in medium without CaCl$_2$. The ejection electrode (seven barrel with a beveled 7-10 micron tip) was placed 75-150 microns away from the recording electrode (1.0-1.5 meg. ohm, 2M NaCl. Time (1-3 sec.) and pressure (1.5-4.5 psi) were adjusted to evoke a 1-2 millivolt negative focal potential. Control ejections of medium without CaCl$_2$ at 2X the highest pressure for 2X the maximal time was routinely performed to insure against pressure artifacts. Electrophysiological recordings were amplified on a WPI KS-700 amplifier. The EPSP signal was stored in a Gould Waveform Storage Module and output to a Gould ES1000 electrostatic recorder for high resolution plotting. The DC signal was sent to the ES1000 Electrostatic Recorder in real time. Results: IC$_{50}$ (vs. NMDA) Example VI: 4 $\mu$M

In Vitro Cultured Hippocampal Cell Assays

Hippocampal neurons were obtained from embryonic day 17 Sprague-Dawley rats. The brains were removed and the hippocampus dissected, placed in ice-cold Leibovitz L-15 medium, carefully stripped of any remaining meninges, and minced into small pieces using scissors. The tissue was rinsed with calcium-magnesium-free Hanks' Balanced Salt Solution and incubated with 0.25% trypsin (Worthington), 40 $\mu$g/ml DNAase (Sigma) for 30 minutes at 36° C. Following incubation, the cells were rinsed with 10% serum-containing medium and dissociated by gentle trituration using a reduced bore diameter Pasteur pipet. The cells were plated on a polylysine-coated (0.5 rg/ml, Sigma) 96-well microtiter plates at 30,000 cells/well. Cells were maintained in fluorodeoxyuridine (5 $\mu$M) containing chemically defined medium [Bottenstein, J., Sato, G., "Growth of a Rat Neuroblastoma Cell Line in Serum-free Supplemented Medium", *Proc. Nat'l. Acad. Sci.*, 76, 514-517 (1979)]until use.

The neuronal survival assay utilized the compound MTT [3-(4,5-dimethylthiazol-2-yl)-2,5-diphenyl tetrazolium bromide], a pale yellow substrate that is cleaved by the mitochondrial enzyme succinate-dehydrogenase to yield a dark blue formazan product. This process requires active mitochondria, present only in live cells. Cultures of hippocampal neurons grown in 96-well plates were incubated with 1 mg/ml MTT at 36° C. in a 10% CO$_2$-in-air incubator for 30-60 minutes. At the end of the incubation, a dark blue precipitate outlined only viable cells. The precipitate was then solubilized using 0.08N HCl/isopropanol mixture and the absorbance measured with an ELISA plate reader (Dynatech MR600) using a test wavelength of 570 nm and a reference wavelength of 630 nm. The resulting optical density is directly proportional to the number of viable cells.

Hypoxia Survival Assay

The compound of Example VI was tested for its ability to protect hippocampal neurons from hypoxia-induced cell death. Cultures of hippocampal neurons were prepared from embryonic day 17 Sprague-Dawley rats. The hippocampi were dissociated into a single cell suspension by incubation with 0.25% trypsin, 40 $\mu$g/ml DNAase followed by gentle trituration through a Pasteur pipet. The cells were plated in a polylysine-coated 96-well plate and maintained in a chemically defined medium until use.

The cells were grown for 2-3 weeks in 5% CO$_2$-in-air humidified environment at 36° C. to establish a thick network of neuronal processes with numerous spontaneously active synapses. Exposure to hypoxic/anoxic environment was accomplished by placing the cultures in an anaerobic chamber, and flushing it with a mixture 95% N$_2$, 5% CO$_2$ gas to rapidly drop the O$_2$ tension to near zero. The O$_2$ tension was maintained at near zero using a disposable H$_2$+CO$_2$ generator envelope with palladium catalyst. The compound of Example VI was added to the culture medium prior to incubation in the anaerobic chamber and maintained there for 6 hours. Following 2 hours of exposure to normal O$_2$ tension, the cultures were processed for morphological and quantitive biochemical neuronal cell viability assays. Maximum protection of neurons from hypoxic insult was obtained with 50 $\mu$M compound of Example VI:

TABLE III

HYPOXIA SURVIVAL DATA

| Sample | Optical Density Units ∓ SDM |
|---|---|
| Control | 0.163 ∓ .017 |
| Hypoxia | 0.062 ∓ .033 |
| Hypoxia + 5 μM Example VI | 0.147 ∓ .033 |
| Hypoxia + 50 μM Example VI | 0.161 ∓ .033 |

Sodium Azide Toxicity Survival Assay

The compound of Example VI was tested for its ability to protect hippocampal neurons from sodium azide poisoning which selectively kills mature neurons while sparing glial cells. Neuronal cells were prepared and the cell viability assays were performed as described in the chronic hypoxia insult assay, above. Cultures were exposed to 10μM sodium azide for 1 hour either in the presence or absence of the compound of Example VI and immediately thereafter processed for qualitative (morphological) and quantitative viability assay. Under this acute and severe toxicity conditions, 1 μM compound of Example VI afforded the neurons significant protection from all death. (See Table IV.)

TABLE IV

SODIUM AZIDE TOXICITY SURVIVAL DATA

| Sample | Optical Density Units ∓ SDM |
|---|---|
| Control | 0.146 ∓ .013 |
| Sodium azide | 0.085 ∓ .013 |
| Sodium azide + Example VI (1 μM) | 0.148 ∓ .013 |

Glutamate Toxicity Survival Assay

The compound of Example VI was tested for its ability to protect neurons from glutamate-induced neurotoxicity, which selectively kills mature neurons while sparing glial cells Neuronal cells were prepared and cell viability assays were performed as described in the chronic hypoxia insult assay, above. Hippocampal cultures were exposed to 500 μM glutamate for 1 hour either in the presence or absence of the compound of Example VI and immediately thereafter processed for qualitative (morphological) and quantitative viability assay. Significant protection was obtained with 5 μM of the compound of Example VI. (See Table v.)

TABLE V

GLUTAMATE TOXICITY SURVIVAL DATA

| Sample | Optical Density Units ∓ SDM |
|---|---|
| Control | 0.163 ∓ .017 |
| Glutamate | 0.092 ∓ .017 |
| Glutamate + 5 μM Example VI | 0.146 ∓ .017 |

In Vivo 3-MPA-Induced Convulsions

In the CD-1 mouse, i.p. injection of 3-MPA produces clonic seizures, tonic hindlimb extension and death. Seizures begin within 2-3 minutes after injection. The dose-response for induction of tonus by 3-MPA is unusual. The incidence of tonus increases rapidly from 35 to 50 mg/kg and remains constant at a less than maximal level over a broad dose range. 3-MPA doses from 50 to 150 mg/kg produce tonus in approximately 75% of the treated mice. The incidence of death over this dose range is variable and less than maximal.

In order to test for antagonism of 3-MPA-induced tonus, the lowest dose of 3-MPA that produced tonus consistently in 75% of the animals (50 mg/kg i.p.) was chosen. Test compounds were administered subcutaneously 30-40 minutes prior to i.p. administration of 3-MPA. Immediately after 3-MPA administration, each mouse was placed in a small cage made of steel rods. The mice were then observed for the presence or absence of tonic hindlimb extension. Reduction (from 75%) in the incidence of tonic hindlimb extension was considered protection from 3-MPA-induced convulsions. The dose of the test compound varied using groups of ten mice per dose until dose response curves are constructed, and $ED_{50}$'s are calculated.

| Results: | 3-MPA Convulsions | s.c. ($ED_{50}$) | i.g. ($ED_{50}$) |
|---|---|---|---|
|  | Ex. VI Compound | 6 mg/kg | 300 mg/kg |

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a dispersion of active compound in hydroxypropylmethyl cellulose.

Formulations for parenteral administration may be in the form of aqueous or non-aqueous isotonic sterile injection solutions or suspensions. These solutions and suspension may be prepared from sterile powders or granules having one or more of the carriers or diluents mentioned for use in the formulations for oral administration.

Although this invention has been described with respect to specific embodiments, the details of these embodiments are not be construed as limitations. Various equivalents, changes and modifications may be made without departing from the spirit and scope of this invention, and it is understood that such equivalent embodiments are part of this invention.

What is claimed is:

1. A method to control neuropathological processes and the neurodegenerative consequences thereof in mammals, which method comprises treating a mammal susceptible to neurologic injury with an effective amount of a compound of the formula

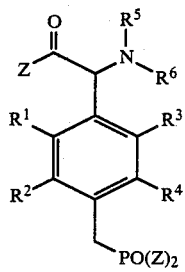 (I)

wherein each of $R^1$ through $R^4$ is independently selected from hydrido, alkyl, cycloalkyl, aralkyl, aryl, haloalkyl, halo, cyano, nitro, and groups represented by —$OR^5$, —$SR^5$,

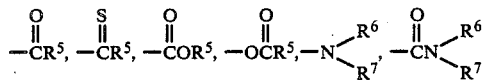

wherein each $R^5$ is independently selected from hydrido, alkyl, aryl, and aralkyl; and wherein each of $R^6$ and $R^7$ is independently selected from hydrido, alkyl, acyl, aryl, aralkyl and

and wherein Z is selected from —$OR^5$, —$SR^5$,

and

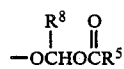

wherein each of $R^5$, $R^6$ and $R^7$ defined as before; with the proviso that $R^6$ and $R^7$ are not at the same time carbonyl-containing groups; and wherein $R^8$ is selected from hydrido and alkyl; or a pharmaceutically-acceptable salt thereof.

2. The method of claim 1 wherein Z is hydroxyl.
3. The method of claim 2 wherein $R^6$ is hydrido.
4. The method of claim 3 wherein at least one of the substituents $R^1$, $R^2$, $R^3$ and $R^4$ are hydrido.

5. The method of claim 4 wherein two or more of the substituents $R^1$, $R^2$, $R^3$ or $R^4$ are hydrido.
6. The method of claim 5 wherein three or more substituents $R^1$, $R^2$, $R^3$ or $R^4$ are hydrido.
7. The method of claim 6 wherein each of the substituents $R^1$, $R^2$, $R^3$, $R^4$ and $R^5$ is hydrido.
8. The method of claim 1 wherein each of the substituents $R^1$, $R^2$, $R^3$ or $R^4$ is independently selected from hydrido, halo, alkyl, alkoxy and thioalkoxy.
9. The method of claim 8 wherein two or more of the substituents $R^1$, $R^2$, $R^3$ or $R^4$ are hydrido.
10. The method of claim 8 wherein three or more of there of the substituents $R^1$, $R^2$, $R^3$ or $R^4$ are hydrido.
11. The method of claim 36 wherein each of the substituents $R^1$, $R^2$, $R^3$ and $R^4$ are hydrido.
12. The method of claim 8 wherein said compound is 4-(phosphonomethyl)phenylglycine.
13. The method of claim 8 wherein said compound is 4-(Ethyl phosphonomethyl)phenylglycine.
14. The method of claim 8 wherein said compound is 2,5-dimethyl-4-(phosphonomethyl)phenylglycine hydrochloride.
15. A compound of the formula

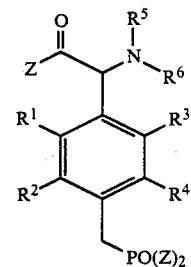 (I)

wherein each of $R^1$ through $R^4$ is independently selected from hydrido, alkyl, cycloalkyl, aralkyl, aryl, haloalkyl, halo, cyano, nitro, and groups represented by —$OR^5$, —$SR^5$

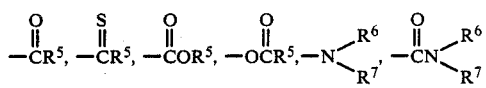

wherein each $R^5$ is independently selected from hydrido, alkyl, aryl, and aralkyl; and wherein each of $R^6$ and $R^7$ is independently selected from hydrido, alkyl, acyl, aryl, aralkyl and

and wherein Z is selected from —$OR^5$, —$SR^5$,

and

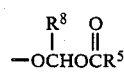

wherein each of $R^5$, $R^6$ and $R^7$ is defined as before; with the proviso that $R^6$ and $R^7$ are not at the same time carbonyl-containing groups; and wherein $R^8$ is selected from hydrido and alkyl; or a pharmaceutically-acceptable salt thereof.

16. Compound of claim 15 wherein Z is hydroxyl.

17. Compound of claim 16 wherein $R^6$ is hydrido.

18. Compound of claim 17 wherein at least one of the substituents $R^1$, $R^2$, $R^3$ and $R^4$ is hydrido.

19. Compound of claim 18 wherein two or more of the substituents $R^1$, $R^2$, $R^3$ or $R^4$ are hydrido.

20. Compound of claim 19 wherein three or more substituents $R^1$, $R^2$, $R^3$ or $R^4$ are hydrido.

21. Compound claim 20 wherein each of the substituents $R^1$, $R^2$, $R^3$, $R^4$ and $R^5$ is hydrido.

22. Compound of claim 15 wherein each of the substituents $R^1$, $R^2$, $R^3$ or $R^4$ is independently selected from hydrido, halo, alkyl, alkoxy and thioalkoxy.

23. Compound of claim 22 wherein two or more of the substituents $R^1$, $R^2$, $R^3$ or $R^4$ are hydrido.

24. Compound of claim 22 wherein three or more of the substituents $R^1$, $R^2$, $R^3$ or $R^4$ are hydrido.

25. Compound of claim 22 wherein each of the substituents $R^1$, $R^2$, $R^3$ and $R^4$ is hydrido.

26. Compound of claim 22 which is 4-(phosphonomethyl)phenylglycine.

27. Compound of claim 22 which is 4-(Ethyl phosphonomethyl)phenylglycine.

28. Compound of claim 22 which is 2,5-dimethyl-4-(phosphonomethyl)phenylglycine hydrochloride.

29. A pharmaceutical composition comprising a therapeutically-effective amount of a compound and a pharmaceutically-acceptable carrier or diluent, said compound selected from a family of compounds of the formula

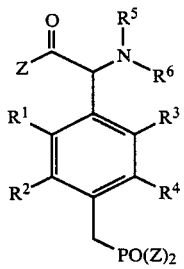

(I)

wherein each of $R^1$ through $R^4$ is independently selected from hydrido, alkyl, cycloalkyl, aralkyl, aryl, haloalkyl, halo, cyano, nitro, and groups represented by —$OR^5$, —$SR^5$,

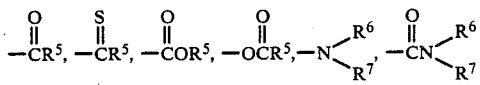

wherein each $R^5$ is independently selected from hydrido, alkyl, aryl, and aralkyl; and wherein each of $R^6$ and $R^7$ is independently selected from hydrido, alkyl, acyl, aryl, aralkyl and

and wherein Z is selected from —$OR^5$, —$SR^5$,

and

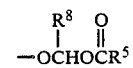

wherein each of $R^5$, $R^6$ and $R^7$ is defined as before; with the proviso that $R^6$ and $R^7$ are not at the same time carbonyl-containing groups; and wherein $R^8$ is selected from hydrido and alkyl; or a pharmaceutically-acceptable salt thereof.

30. The composition of claim 29 wherein Z is hydroxyl.

31. The composition of claim 30 wherein $R^6$ is hydrido.

32. The composition of claim 31 wherein at least one of the substituents $R^1$, $R^2$, $R^3$ and $R^4$ is hydrido.

33. The composition of claim 32 wherein two or more of the substituents $R^1$, $R^2$, $R^3$ or $R^4$ are hydrido.

34. The composition of claim 33 wherein three or more substituents $R^1$, $R^2$, $R^3$ or $R^4$ are hydrido.

35. The composition claim 34 wherein each of the substituents $R^1$, $R^2$, $R^3$, $R^4$ and $R^5$ is hydrido.

36. The composition of claim 29 wherein each of the substituents $R^1$, $R^2$, $R^3$ or $R^4$ is independently selected from hydrido, halo, alkyl, alkoxy and thioalkoxy.

37. The composition of claim 36 wherein two or more of the substituents $R^1$, $R^2$, $R^3$ or $R^4$ are hydrido.

38. The composition of claim 36 wherein three or more of the substituents $R^1$, $R^2$, $R^3$ or $R^4$ are hydrido.

39. The composition of claim 36 wherein each of the substituents $R^1$, $R^2$, $R^3$ and $R^4$ is hydrido.

40. The composition of claim 36 wherein said compound is 4-(phosphonomethyl)phenylglycine.

41. The composition of claim 36 wherein said compound is 4-(ethyl phosphonomethyl)phenylglycine.

42. The composition of claim 36 wherein said compound is 2,5-dimethyl-4-(phosphonomethyl)phenylglycine hydrochloride.

* * * * *